US010993777B2

(12) United States Patent
Nowatschin et al.

(10) Patent No.: US 10,993,777 B2
(45) Date of Patent: May 4, 2021

(54) METHOD AND APPARATUS FOR CONTROLLING A SURGICAL MECHATRONIC ASSISTANCE SYSTEM BY MEANS OF A HOLDING ARM FOR MEDICAL PURPOSES

(71) Applicant: Brainlab Robotics GMBH, Munich (DE)

(72) Inventors: Stephan Nowatschin, Munich (DE); Maximilian Krinninger, Weßling-Oberpfaffenhofen (DE); Dominikus Gierlach, Munich (DE)

(73) Assignee: Brainlab Robotics GMBH, Munich (DE)

( * ) Notice: Subject to any disclaimer, the term of this patent is extended or adjusted under 35 U.S.C. 154(b) by 113 days.

(21) Appl. No.: 15/561,042

(22) PCT Filed: Mar. 23, 2016

(86) PCT No.: PCT/EP2016/056459
§ 371 (c)(1),
(2) Date: Sep. 23, 2017

(87) PCT Pub. No.: WO2016/156168
PCT Pub. Date: Oct. 6, 2016

(65) Prior Publication Data
US 2018/0071049 A1   Mar. 15, 2018

(30) Foreign Application Priority Data
Mar. 27, 2015 (DE) .................... 10 2015 104 810.8

(51) Int. Cl.
*A61B 34/30* (2016.01)
*A61B 90/50* (2016.01)
(Continued)

(52) U.S. Cl.
CPC .......... *A61B 90/50* (2016.02); *A61B 1/00149* (2013.01); *A61B 90/37* (2016.02);
(Continued)

(58) Field of Classification Search
CPC ..... A61B 90/50; A61B 1/00149; A61B 90/37; A61B 2017/00115; A61B 2017/00207;
(Continued)

(56) References Cited

U.S. PATENT DOCUMENTS 6,400,352 B1 *  6/2002  Bruneau .................. G09B 9/28
345/156
6,569,084 B1 *  5/2003  Mizuno .............. A61B 1/00149
248/325
(Continued)

FOREIGN PATENT DOCUMENTS

EP   1520548 A2   4/2005
EP   1557134 A1   7/2005
(Continued)

*Primary Examiner* — Stephen Holwerda
(74) *Attorney, Agent, or Firm* — BakerHostetler

(57) ABSTRACT

A holding arm for medical purposes, in particular for holding a mechatronic assistance system, includes a proximal end for attaching the holding arm to a base and a distal end for receiving the surgical mechatronic assistance system, an assistance interface at the distal end for coupling the holding arm to the assistance system to control the assistance system, an assistance operating device designed to detect an operator action by an operator which is directed at controlling the assistance system and if necessary to transmit a request signal representing the operator action to the assistance interface for the purpose of controlling the surgical mechatronic assistance system.

29 Claims, 8 Drawing Sheets

(51) Int. Cl.
  *A61B 90/00* (2016.01)
  *A61B 1/00* (2006.01)
  *A61B 17/00* (2006.01)
  *A61B 34/20* (2016.01)
(52) U.S. Cl.
  CPC .............. *A61B 34/20* (2016.02); *A61B 34/30* (2016.02); *A61B 2017/00115* (2013.01); *A61B 2017/00207* (2013.01); *A61B 2090/508* (2016.02)
(58) Field of Classification Search
  CPC .... A61B 34/20; A61B 34/30; A61B 2090/508
  See application file for complete search history.

(56) References Cited

U.S. PATENT DOCUMENTS

| | | | |
|---|---|---|---|
| 7,841,979 B2 | 11/2010 | Hirose | |
| 2002/0111701 A1* | 8/2002 | Borders | A61H 9/0078 700/60 |
| 2004/0024311 A1* | 2/2004 | Quaid, III | A61B 34/10 600/428 |
| 2004/0128026 A1* | 7/2004 | Harris | A61B 34/76 700/245 |
| 2005/0154295 A1* | 7/2005 | Quistgaard | A61B 8/00 600/424 |
| 2005/0209614 A1 | 9/2005 | Fenter et al. | |
| 2007/0129846 A1 | 6/2007 | Birkenbach et al. | |
| 2014/0039681 A1* | 2/2014 | Bowling | B25J 13/00 700/261 |
| 2014/0222023 A1 | 8/2014 | Kim et al. | |
| 2015/0216489 A1* | 8/2015 | Everaerts | A61B 6/12 600/424 |
| 2015/0265807 A1* | 9/2015 | Park | A61B 34/25 600/424 |
| 2015/0293596 A1* | 10/2015 | Krausen | A61B 34/30 606/130 |

FOREIGN PATENT DOCUMENTS

| | | |
|---|---|---|
| EP | 1577134 A1 | 7/2005 |
| EP | 2047805 A1 | 4/2009 |
| WO | 2011085815 A1 | 7/2011 |
| WO | 2014151550 A2 | 9/2014 |

\* cited by examiner

METHOD AND APPARATUS FOR CONTROLLING A SURGICAL MECHATRONIC ASSISTANCE SYSTEM BY MEANS OF A HOLDING ARM FOR MEDICAL PURPOSES

CROSS-REFERENCE TO RELATED APPLICATIONS

This application is a National Stage of International Patent App No. PCT/EP2016/056459, filed Mar. 23, 2016, which claims priority to German Patent App. No. DE 10 2015 104810.8, filed Mar. 27, 2015, the disclosures of which are incorporated by reference in their entirety.

FIELD OF THE INVENTION

The invention relates to a holding arm for medical purposes, in particular for holding a surgical mechatronic assistance system comprising a proximal end for attaching the holding arm to a base and a distal end for receiving a surgical mechatronic assistance system. The invention further relates to a method for controlling a mechatronic assistance system, in particular using such a holding arm.

BACKGROUND

Holding arms of the kind initially specified have long been known from the prior art and are specifically used in surgery to relieve an operator of static holding work. Such a holding arm is used to hold a mechatronic assistance system and/or a surgical instrument, for example a manipulator, an endoscope, a surgical clamp or the like. The holding arms initially specified have proved their usefulness for holding endoscopes, in particular. In endoscopic surgery, an operator generally operates an instrument with both hands, while an assistant holds the endoscope in order to make the operating area visible on a screen. Holding the endoscope over a protracted period is very tiring. Holding arms are increasingly used for that reason.

Such a holding arm and such a method are described, for example, in the as yet unpublished patent application no. DE 10 2014 016 823.9. A holding arm having an operating device is described therein, the operating device being designed to bring the holding arm into a desired pose and also being designed to release the associated joint upon contact between an operator and one of the first and second arm segments.

SUMMARY OF THE INVENTION

The object of the present invention is to provide a holding arm and a method that have greater versatility.

This object is achieved in respect of the holding arm by a holding arm for medical purposes, in particular for holding a mechatronic assistance system, comprising a proximal end for attaching the holding arm to a base and a distal end for receiving the surgical mechatronic assistance system; an assistance interface at the distal end for coupling the holding arm to the assistance system in order to control the assistance system; and an assistance operating device designed to detect an operator action by an operator which is directed at controlling the assistance system and if necessary to transmit a request signal representing the operator action to the assistance interface for the purpose of controlling the surgical mechatronic assistance system.

The foundations have now been laid, advantageously, for controlling a servodrive of a mechatronic assistance system connected to the assistance interface, by performing an operator action, for example a contact-based and/or contactless finger gesture. Assistance systems within the meaning of the invention are understood to be any kind of mechatronic manipulators which are used in surgery, such as endoscopes, exoscopes, laparoscopes, trocars and the like. The assistance interface at the distal end of the holding arm is designed to couple mechanically with the assistance system in order to hold the latter in a defined position relative to the holding arm, and also to provide the other connections that are necessary, such as a connection for electrical energy and a connection for transmitting signals, in particular request signals.

The assistance operating device may be provided in different configurations. For example, the assistance operating device may have contacting devices which are provided so that an operator comes into contact with them. A contacting device is advantageously provided in the form of a touch-sensitive sensor, preferably as a touch-sensitive sensor array. By that means, an operator can trace motion paths with his finger, for example, which are detected as a chronological series of coordinates and which can be processed by a processor unit of the holding arm. It is thus possible, for example, to implement contact-based gesture control of a mechatronic assistance system connected to the assistance interface. The assistance operating device may be designed to drive a connected mechatronic assistance system proportionally to an operator action in the form of a motion path. For example, the assistance operating device may be designed to extend a connected endoscope (mechatronic assistance system) a distance of 1 cm when a finger is moved in a straight line by 1 cm. It should be understood that such control can be "translated" by a proportionality factor, such that a connected endoscope extends a distance of 2 cm when a finger is moved in a straight line by 1 cm, or vice versa.

The contacting device may be provided in the form of a pushbutton or a button. A contacting device in the form of a pushbutton or button may be provided, for example, to make the assistance operating device output a predefined request signal ("Move to end position"; "Rotate 90 degrees", etc.). The assistance operating device may be designed to determine what kind of assistance system is coupled to the holding arm. The assistance operating device is preferably designed to assign a controller function to a contacting device, depending on the type of assistance system that is detected.

Alternatively or additionally, the assistance operating device has a detection unit for detecting the operator action contactlessly. This has advantages for sterility, inter alia, in that an operator does not need to touch the holding arm in order to control the assistance system. The detection unit preferably has a camera and/or a distance sensor. The camera is provided in the form of a CCD camera, for example, whereas the distance sensor is provided in the form of a capacitive sensor, for example. The contact-based gesture control described above with reference to the touch-sensitive sensor array may likewise be implemented as contactless gesture control by means of the detection unit for detecting the operator action contactlessly.

The contacting device and the detection unit for contactless detection of the operator action may be provided in redundant form, and the assistance operating device may preferably be configured to verify whether an operator action directed at controlling the assistance system, in particular a gesticular operator action by an operator, is actually being performed.

According to another preferred configuration, the assistance operating device has at least one control ring. The control ring may be arranged around the circumference of at least one arm segment of the holding arm and/or is axially mobile. If the holding arm has a plurality of arm segments, a control ring or some other kind of assistance operating device may be provided for each arm segment. Alternatively or additionally thereto, two or more control rings are provided on one arm segment.

It is particularly preferred that the holding arm has a processor unit which is assigned to the assistance operating device and configured to translate the operator action into a data structure. The processor unit is preferably coupled in communication, at least for periods, with the contacting device, the detection unit and/or the control ring, in particular for transmitting coordinates and the time they were recorded. A communicative coupling may be provided, for example, by a serial interface or the like. A separate processor unit is preferably assigned to each arm segment on which an assistance operating device is arranged.

The processor unit is preferably configured to translate the operator action into a data structure comprising a 3D motion vector and/or a velocity value. It is preferred that the processor unit is configured to translate at least two successive coordinates into a 3D motion vector (direction vector). The processor unit is also preferably configured to calculate a speed of motion from the detection times of the at least two successive coordinates. The processor unit is preferably configured to convert the data structure into the request signal for the assistance system. Alternatively, the data structure itself is sent as a request signal to the assistance system.

In another preferred embodiment, the holding arm is equipped with a base interface at that proximal end for connecting the holding arm to an external control unit for transmitting signals to and from the holding arm. The holding arm preferably has a transmission means which is arranged inside the holding arm and which connects the assistance interface to the base interface in order to transmit signals between the interfaces.

The transmission means preferably has means for transmitting electrical energy. Any cables that are required in order to transmit electrical energy and/or data from the base interface to the assistance interface are thus arranged inside the holding arm arranged and are thus protected during operation of the holding arm. The basis interface and/or the assistance interface preferably have transmission means for transmitting the data captured by the sensor or sensors. These transmission means preferably include interfaces, such as Bluetooth®, USB, RS-232 or similar. The transmission means preferably has a bus system.

The holding arm preferably has a plurality of arm segments and a plurality of joints by means of which the arm segments are connected to each other by articulated joints. The holding arm preferably has at least six arm segments and at least six joints. The arm segments themselves are substantially rigid and preferably rod-shaped. The expression "rod-shaped" here includes not only substantially straight arm segments, but also slightly or strongly curved arm segments. In such a holding arm, arm segment and joints always alternate. The holding arm is preferably configured as a passive holding arm, so called, and for that reason has joints which are actively braked exclusively, but not driven joints as is often the case with robotic holding arms. Each joint is therefore releasable and lockable only, but cannot be driven. As a result, the holding arm is simple in design and does not need a complex controller in order to operate it. The holding arm may be manually adjustable, in that the individual joints are adjusted against the braking force of the brakes.

According to another preferred embodiment, the holding arm has six degrees of freedom. It is particularly preferred that the holding arm has seven degrees of freedom. Whereas six degrees of freedom are sufficient to reach any point in space, it is possible with seven degrees of freedom to reach any point with different poses, so the holding arm can always be oriented in such a way that the operating area is easily accessible, for example. For that reason, it is particularly preferred that the holding arm has seven degrees of freedom.

According to one preferred embodiment, the holding arm has seven arm segments and seven joints, with each arm segment being assigned one joint. According to this embodiment, each joint preferably has one degree of freedom, so the holding arm has a total of seven degrees of freedom. It is also possible that each joint has two or more degrees of freedom, with joints having one degree of freedom being preferable on account of their stability. All the joints are preferably designed as rotary joints. It is preferable that some of the joints are designed as rotary joints and some as translational joints. When the joints are all designed as rotary joints, they are preferably disposed in the holding arm in such a way that axes of successive joints along the holding arm, from the proximal to the distal end of the holding arm, are perpendicular to each other.

It has been found to be advantageous if the assistance operating device is arranged on or in at least one of the arm segments. The assistance operating device may be distributed across several arm segments. The processor unit is preferably coupled at least temporarily to the transmission means and is configured to fetch sensor data and/or workspace data relating to the holding arm from the transmission means. The sensor data relating to the holding arm may originate from sensors of the holding arm, for example from orientation sensors.

In another preferred embodiment, the holding arm has an orientation sensor in at least one joint, for detecting an attitude of the joint. An orientation sensor for detecting the attitude of a joint is preferably disposed in every joint. Such an orientation sensor may be in the form of a capacitive displacement sensor, for example, which mechanically senses a path of joint movement and in that way determines an angular position, or in the form of an acceleration sensor which detects spatial movement of the joint. In addition or alternatively thereto, motion sensors are provided in the arm segments so that the spatial position of the arm segments can be determined. By this means, it is possible to define a holding arm pose which can then be provided to the assistance system and/or to the external control unit via the base interface and/or the assistance interface. This is particularly advantageous when an OP navigation system is used and the latter uses the information about the pose of the holding arm in order to coordinate navigation. It is also possible to determine, via the pose of the holding arm, whether a collision with other devices or with the holding arm itself is liable to occur. The safety of the holding arm is further improved as a result.

If an acceleration sensor is used as the orientation sensor, it is also possible to detect movement of the holding arm as a whole, without changing the pose. For example, if the operating table moves during the operation, the holding arm can detect that movement. The holding arm may be adapted to emit a warning signal when the operating table reaches a particular inclination, for example from 15 degrees onwards. If an inclination of the operating table is set too steeply, it is possible that a patient on the operating table will slide along the operating table, and this may cause injuries. For example, if an endoscope which is introduced into a patient's nose, for example, is disposed at the assistance interface of the holding arm, and if the inclination of the table is then adjusted, the holding arm detects the inclination of the table by means of the motion sensors, and also, by means of torque sensors in the joints, any change in the load acting on the endoscope, which may likewise be an indication that the patient on the operating table is sliding.

In another preferred embodiment, a torque sensor is disposed in at least one joint to detect a torque acting on said joint. Such a torque sensor is preferably disposed in all the joints. By detecting the torques acting on the joints, it is possible to determine a force that is acting at the distal end of the holding arm. In that way, it is possible to determine the weight of an assistance system which is coupled to the distal end. It is also possible when using the holding arm to determine forces acting upon it. It is conceivable, for example, that an endoscope is disposed at the assistance interface. When handling the endoscope, for example when introducing the endoscope into a body orifice of a patient, it is possible to determine a resistance encountered by the endoscope. It is possible in that way to identify whether there is any risk of the patient being injured. The captured torque data are preferably supplied to the processor unit.

It has been found to be advantageous if the processor unit is configured to take the sensor data relating to the holding arm into account when translating the operator action into the data structure. It is particularly preferred that the processor unit be configured to detect whether the surgical mechatronic assistance system would remain within a permitted workspace when driven in accordance with the request signal. According to another preferred variant, the processor unit is configured to cause the request signal to be transmitted to the surgical mechatronic assistance system only if the surgical mechatronic assistance system would remain within a permitted workspace when driven in accordance with the request signal.

It may also be arranged that a previously adopted position of an assistance system, in particular of an endoscope, is excluded from the permitted workspace and accordingly can no longer be adopted. Injuries can thus be prevented. The workspace data relating to the holding arm may originate, for example, from an external control unit connected via the base interface and forming part of an OP navigation system. Alternatively or additionally, the workspace data may be provided in the form of a planning file, a DICOM file or the like.

The operating device may have signalling means for emitting a warning signal which is perceptible to the operator. The processor unit is preferably configured to activate the signalling means if the surgical mechatronic assistance system would leave the permitted workspace and/or would approach a workspace boundary to within a predefined distance when driven in accordance with the request signal. The signalling means may be provided in the form of a vibration module and/or as a visual display module. The processor unit may be configured to drive the signalling means according to the distance of the assistance system from the workspace boundary, for example with a control current that is inversely proportional to the distance.

It is particularly preferred if, in addition to the assistance operating device, the holding arm has an arm operating device for bringing the holding arm into a desired pose. The arm operating device is preferably designed to release the associated joint upon contact between an operator and an arm segment. This is specifically preferred when the holding arm is designed as a passive holding arm with joints which are actively braked, so it is preferably arranged that when an operator comes into contact with a respective arm segment, only the associated joint is released. This makes it possible to move individual joints intuitively and thus to adjust the holding arm segment by segment and to bring it into a desired pose. By this means, positioning can be carried out with greater precision, because each segment can be separately adjusted incrementally. It is likewise possible to contact a plurality of arm segments at once, with the result that a plurality of joints can be released and thus adjusted simultaneously. This allows the holding arm to be brought into a desired pose in a simple manner, and in particular intuitively. A contacting device may be provided for that purpose on the holding arm, in particular on the segments, and cooperates with the arm operating device in such a way that the arm operating device releases an associated joint upon contact between the operator and the contacting device.

In another preferred embodiment of the invention, the joints have brakes by means of which the joints can be released and locked. The purpose of the brakes is to brake or prevent movement of the arm segments relative to each other, i.e. to brake or prevent any movement of the joints. If the brakes are released, the joints are released.

The object of the invention is similarly achieved with a system comprising a holding arm as described in the foregoing and a surgical mechatronic assistance system.

This object is achieved in respect of the method by a method for controlling a surgical mechatronic assistance system coupled to a holding arm for medical purposes, comprising the steps of:

detecting an operator action by an operator which is directed at controlling the assistance system, by means of an operating device arranged on the holding arm, and transmitting, if necessary, a request signal representing the operator action to the assistance interface for the purpose of controlling the surgical mechatronic assistance system.

Transmitting the request signal to the assistance interface "if necessary" should be understood in the present context to mean that the request signal need not necessarily be transmitted for each and every operator action. Instead, transmission is preferably bound to conditions, such as the mechatronic assistance system complying with a workspace restriction as described below.

The request signal is preferably only converted into a control signal for the surgical mechatronic assistance system in the assistance system itself. Alternatively, the request signal is converted into a control signal for the surgical mechatronic assistance system in a processor unit which is assigned to the holding arm and which is preferably provided in the form of a microcontroller. The computing power required in the mechatronic assistance systems can thus be advantageously reduced.

In one preferred embodiment, the method comprises the step of: translating the detected operator action into a data structure, wherein the data structure preferably comprises a motion vector, in particular a 3D motion vector and/or a velocity value. It is particularly preferred that the data structure comprises a 3D motion vector and a velocity value. The request signal is preferably generated from the data structure.

Within the method, the sensor data and/or workspace data relating to the holding arm are preferably fetched via the transmission means. In this way, the control precision and also the resultant safety of the surgical mechatronic assistance system to be controlled in advantageously increased.

The method preferably comprises the step of: translating the detected operator action into a data structure, taking into account the sensor data relating to the holding arm. To that end, the motion vector which is directly representative of the operator action on the operating device arranged on the holding arm, i.e. without the transformation relating to the holding arm, is preferably transformed into a resultant motion vector.

The resultant motion vector is preferably calculated in such a way that a transformation matrix is calculated which represents the momentary spatial position of the assistance operating device, in particular of a contacting device, in relation to a base coordinate system of the holding arm and which preferably has at least one rotational and one translational component of transformation. It is further preferred that a transition matrix is calculated which represents the momentary spatial position of the assistance operating device, in particular of the contacting device, in relation to a operating point of the mechatronic assistance system. It is also preferred that the motion vector of the operating device is multiplied from the right to form the transition matrix, which in turn is multiplied from the right to form the transformation matrix. The transformation matrix is preferably populated with the sensor data relating to the holding arm and with mechanical/design parameters of the holding arm. It is further preferred that the transition matrix is populated with sensor data relating to the mechatronic assistance system and with mechanical/design parameters relating to the mechatronic assistance system.

In another preferred embodiment, the method comprises the step of: detecting whether the surgical mechatronic assistance system would remain within a permitted workspace when driven in accordance with the request signal. The permitted workspace of the surgical mechatronic assistance system is preferably stored in an intraoperative navigation system and/or in a planning file. If, for example, a linear module included in a mechatronic assistance system (e.g. for retracting/extending an endoscope) is steered along a fixed translation axis, then the permitted workspace is preferably defined by the maximum permitted insertion depth of the endoscope.

The request signal is preferably transmitted to the surgical mechatronic assistance system whenever the surgical mechatronic assistance system would remain within a permitted workspace when driven in accordance with the request signal. In that case, a request signal is transmitted only on condition that the workspace boundaries would not be violated by the assistance system.

Alternatively or additionally, the method may comprise the step of: filtering a request signal if the surgical mechatronic assistance system would leave the permitted workspace when driven in accordance with the request signal. The method may include filtering the request signal, if and insofar as the surgical mechatronic assistance system would leave a permitted workspace when driven in accordance with the request signal and/or would approach the boundary of the permitted workspace to within a predefined distance. Filtering "if and insofar" is preferably done by scaling the request signal. The request signal is preferably scaled in respect of a speed by which, for example, a linear module included in a mechatronic assistance system is to be moved. This filtering would manifest itself to an endoscope operator in such a way that the endoscope approaches the boundary of the permitted workspace at a speed specified at the operating device by the operator using gesture control, in order to automatically slow down or stop there.

It is particularly preferred if a warning signal which is perceptible to the operator is emitted via the operating device if the workspace for the surgical mechatronic assistance system is restricted. The warning signal is preferably emitted in conjunction with the boundary of the permitted workspace being approached, as just described.

The method may comprise the step of: determining whether an operator action detected via the operating device is directed at releasing a joint or a movement of the mechatronic assistance system. This is advantageous particularly when the assistance operating device and the arm operating device are operated using one and the same contacting device, for example. Such determining is preferably carried out by analysing speech input from a user, for example by saying the words "release mode joints" or "control mode assistance system".

It is particularly preferred if the operator action or the operator is a gesture, in particular a finger gesture.

It should be understood that the holding arm according to the invention and the method according to the invention have identical and similar aspects as specified, in particular, in the dependent claims. Reference is therefore made to the entire description above in respect of the holding arm for the preferred variants of the method and their respective advantages.

BRIEF DESCRIPTION OF THE DRAWINGS

The invention shall now be described in more detail with reference to three embodiments and with reference to the attached drawings, In the drawings.

DETAILED DESCRIPTION

Figure 1:
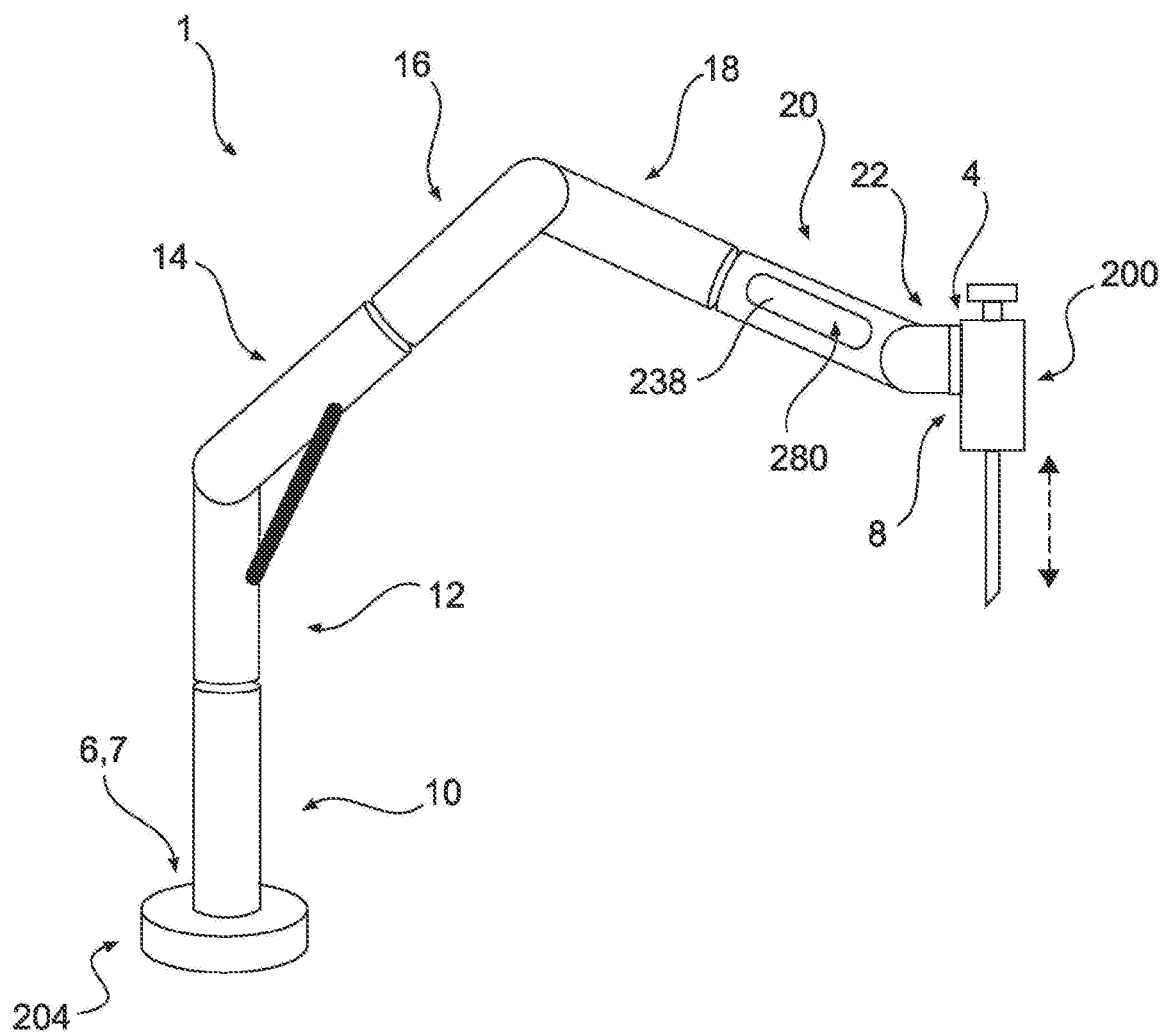
FIG. 1 shows a first embodiment of a holding arm according to the invention.

FIG. 1 shows a holding arm 1 for medical purposes, in particular for holding a surgical mechatronic assistance system 200, which is provided here in the form of a mechatronic endoscope.

Holding arm 1 has a proximal end 2 and a distal end 4. At the proximal end 2, a base interface 6 and a mechanical interface 7 are formed. Mechanical interface 7 is used to attach holding arm 1 to a base 204, for example to an operating table. Base interface 6 is used to transfer energy and to couple holding arm 1 to an external control unit 206 (cf. FIG. 6). At the distal end 4, an assistance interface 8 is provided via which it is possible to couple mechatronic assistance system 200 to holding arm 1 and to control it. The holding arm 1 according to FIG. 1 has seven arm segments 10, 12, 14, 16, 18, 20, 22, each of which is substantially rod-shaped and all of which, except for the last arm segment 22, are of substantially the same length.

Holding arm 1 has an assistance operating device 280 which is arranged on the second-last arm segment 20 and designed to detect operator action by an operator which is directed at controlling the assistance system 200 and if necessary to transmit a request signal representing the operator action to the assistance interface 8 for the purpose of controlling the surgical mechatronic assistance system 200.

FIG. 1 shows, in schematic form and only in parts, a holding arm 1 with a mechatronic assistance system 200 connected to it, said assistance system 200 being coupled via an assistance interface 8 of holding arm 1 to a bus system 76 of holding arm 1. In this embodiment, holding arm 1 has an assistance operating device 280 comprising contacting device 238 in the form of a touch-sensitive sensor array. The contacting device 238, provided as a touch-sensitive sensor array, of assistance operating device 280 supplies coordinates of motion x1, y1; x2, y2; xn, yn on a touch-sensitive surface (not shown) and the respective detection time t1; t2; tn to a serial interface 240 (cf. FIG. 7).

The one assistance operating device 280 has an associated processor unit 100, which has a first microcontroller 110 and a second microcontroller 120 in this example. The two microcontrollers 110, 120 do not necessarily have to be provided as discrete components, but may also be realised by one and the same component. In the present example, the two microcontrollers 110, 120 are provided as discrete components which are coupled in communication via a data link 115.

The first microcontroller 110 of processor unit 100 of holding arm 1 receives the coordinates of motion x1, y1; x2, y2; xn, yn and converts two successive sets of coordinates x1, y1; x2, y2 into an internal data structure (three-dimensional motion vector). The direction of motion r of motion path P that is traced by the operator on the contacting device 238 embodied as a touch-sensitive sensor array is thus defined. If the operator moves only one finger over the contacting device 238 embodied as a touch-sensitive sensor array, then that is a two-dimensional movement and the third coordinate in motion vector r is accordingly 0.

Using the two detection times t1; t2, the first microcontroller 110 calculates a speed of motion v which is transmitted together with motion vector r to the second microcontroller 120. If an operator moves two fingers simultaneously on the contacting device 238 embodied as a touch-sensitive sensor array, two sets of coordinates and detection times are transmitted simultaneously. In the case of three fingers, three sets are transmitted.

If, for example, a linear module included in a mechatronic assistance system 200 is steered along a fixed translation axis (cf. FIG. 1, broken line), then the first microcontroller 110 is preferably configured to generate a motion vector r=(0, 0, 1) when the operator performs a two-finger gesture, for example, on the contacting device 238 embodied as a sensor array, in which the two fingers are moved towards each other until they touch. When transmitted to the mechatronic assistance system 200, if the need arises, motion vector r=(0, 0, 1), converted into a request signal m, would cause the linear module to retract. Accordingly, the first microcontroller 110 must also be preferably configured to generate a motion vector r=(0, 0, −1) if the two fingers are moved away from each other after initially touching each other. When transmitted to the mechatronic assistance system 200, if the need arises, motion vector r=(0, 0, −1), converted into a request signal m, would cause the linear module to extend.

The first microcontroller 110 of processor unit 100 is coupled in communication to an internal bus system 76 that is part of a transmission means arranged inside holding arm 1 and which connects assistance interface 8 to a base interface (not shown) of holding arm 1 for the transmission of signals between the interfaces. The first microcontroller 110 of processor unit 100 is configured here to fetch sensor data (SI1, SI2, SIN) relating to the holding arm over bus system 76. Using those sensor data (SI1, SI2, SIN), the first microcontroller 110 of processor unit 100 calculates the spatial location of the holding arm in order to determine the location of contacting device 238 and to take account of that location when calculating the (resultant) motion vector r.

The resultant motion vector is preferably calculated in such a way that a transformation matrix is calculated which represents the momentary spatial position of contacting device 238 in relation to a base coordinate system of holding arm 1 and which preferably has at least one rotational and one translational transformation component; and/or in such a way that a transition matrix is calculated which represents the momentary spatial position of contacting device 238 in relation to an operating point of the mechatronic assistance system 200; and/or in such a way that the motion vector r of the contacting device, as calculated by the first microcontroller 110, is multiplied from the right to form the transition matrix, which in turn is multiplied from the right to form the transformation matrix.

Motion vector r and speed of motion v form a data structure which is transmitted via data link 115 from the first microcontroller 110 to the second microcontroller 120. The second microcontroller 120 of processor unit 100 is likewise coupled in communication to internal bus system 76 and is configured to submit queries to the internal bus system 76 about whether there are any workspace restrictions (C1, C2, . . . Cn) in a planning file or for example in an intraoperative navigation system. The second microcontroller 120 is also configured to transmit a request signal to assistance interface 8 for the purpose of controlling the surgical mechatronic assistance system 200, if need be. Such a need exists, for example, when the second microcontroller 120 of processor unit 100 determines that the surgical mechatronic assistance system 200 would remain within a permitted workspace when being driven in accordance with the request signal m. In that case, therefore, the request signal m representing the operator action is sent to assistance interface 8 and is converted by the surgical mechatronic assistance system 200 into a control signal for driving internal motors.

If the second microcontroller 120 of processor unit 100 determines that the surgical mechatronic assistance system 200 would leave the permitted workspace if driven in accordance with the request signal (e.g. "endoscope touches the target area in an undesired manner"), then the second microcontroller 120 of assistance operating device 280 emits a warning w, which is converted in signalling means 239 of processor unit 100 into a warning signal which is perceptible to the operator, in this case a warning sound W', for example. In this case, there is no need to transmit request signal m to assistance interface 8, since that might lead to the patient being injured.

Figure 2:
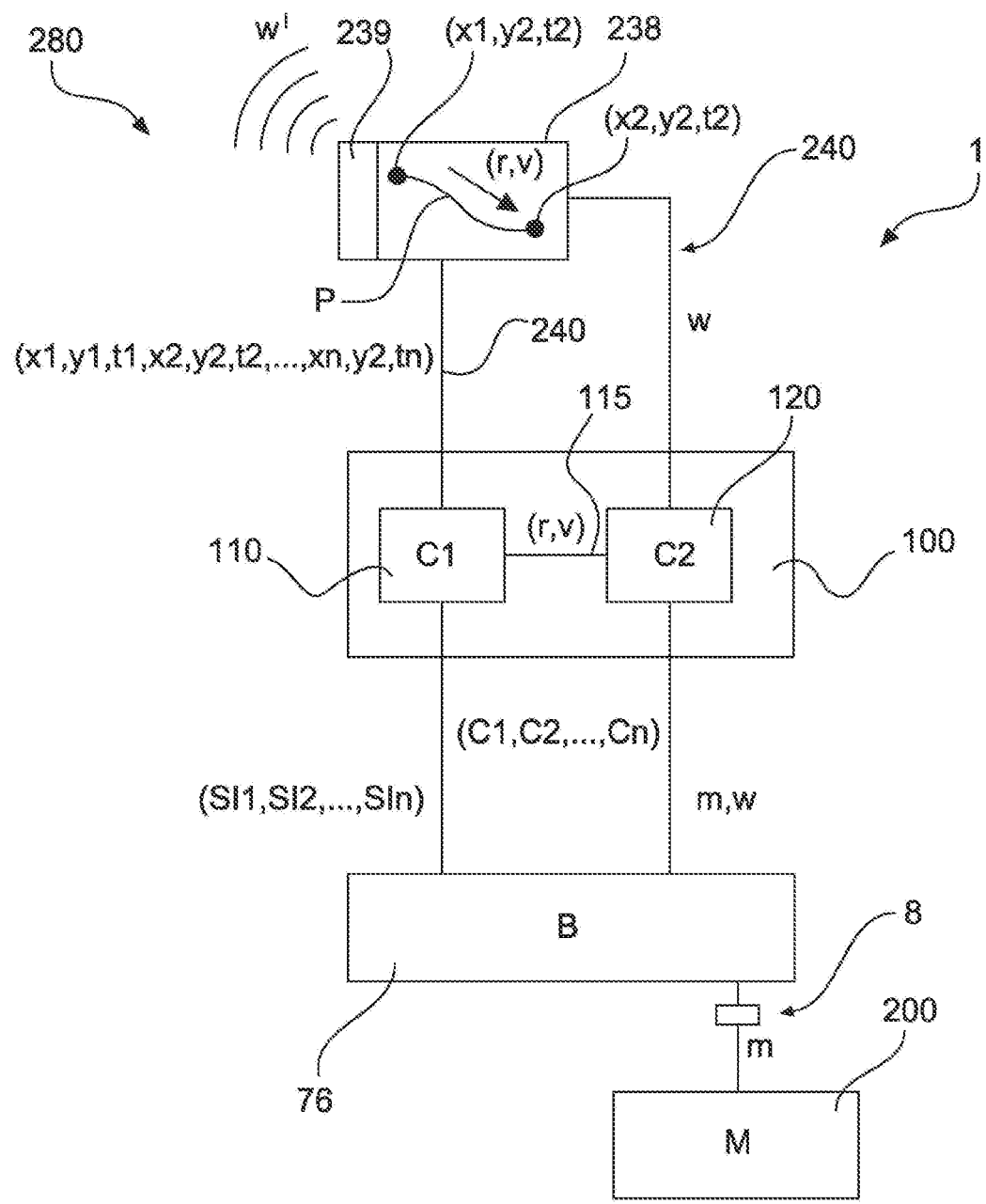
FIG. 2 shows schematically the functional operation of the holding arm according to the invention.
Figure 3:
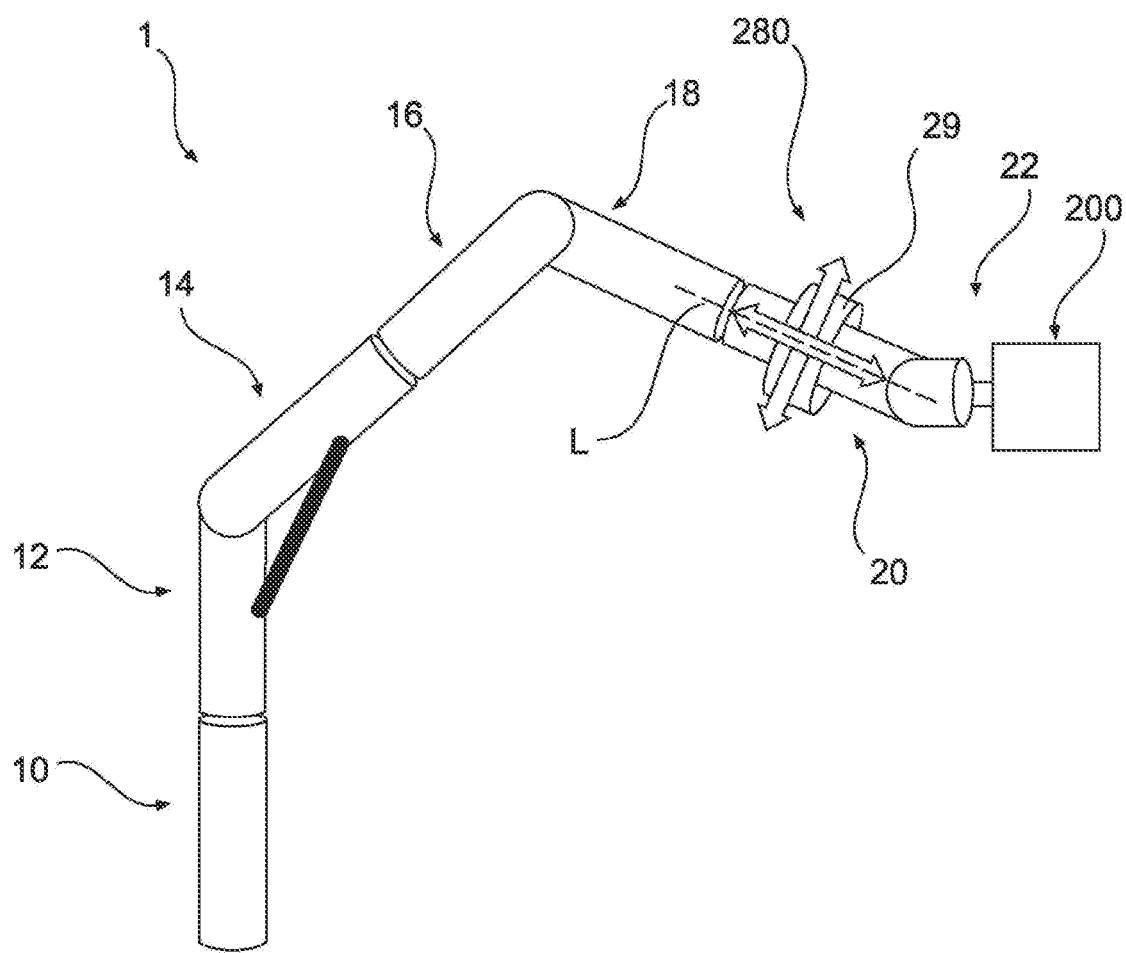
FIG. 3 shows a side view of a holding arm according to a second embodiment, in which a control ring of the assistance operating device can be seen.

FIG. 3 shows a holding arm 1 according to a second embodiment of the invention. Holding arm 1 is substantially identical to the one shown in FIGS. 1 and 2 and has seven arm segments 10, 12, 14, 16, 18, 20, 22. Unlike the previous embodiments, arm operating device 280 of holding arm 1 has a control ring 29. The latter is arranged around the circumference of the second last arm segment 20 and—as indicated by the arrows—is rotatable at least circumferentially about the longitudinal axis L of arm segment 20 and is axially movable along longitudinal axis L.

When operator control ring 29 rotates about longitudinal axis L, this is detected by processor unit 100 (cf. FIG. 2) and a corresponding request signal which can include and/or represent the direction of rotation, the angle of rotation and/or the rotational acceleration is sent via the internal bus system 76 (cf. FIG. 2) to the surgical mechatronic assistance system 200. The control software of assistance system 200 receives the request signal, computes one or more control commands from it, and sends these to the motors (not shown) of assistance system 200. If the operator moves control ring 29 back or forth along longitudinal axis L, processor unit 100 detects this and sends the direction of motion and the path travelled and the speed of movement and the acceleration via the internal bus system 76 to assistance system 200.

Figure 4:
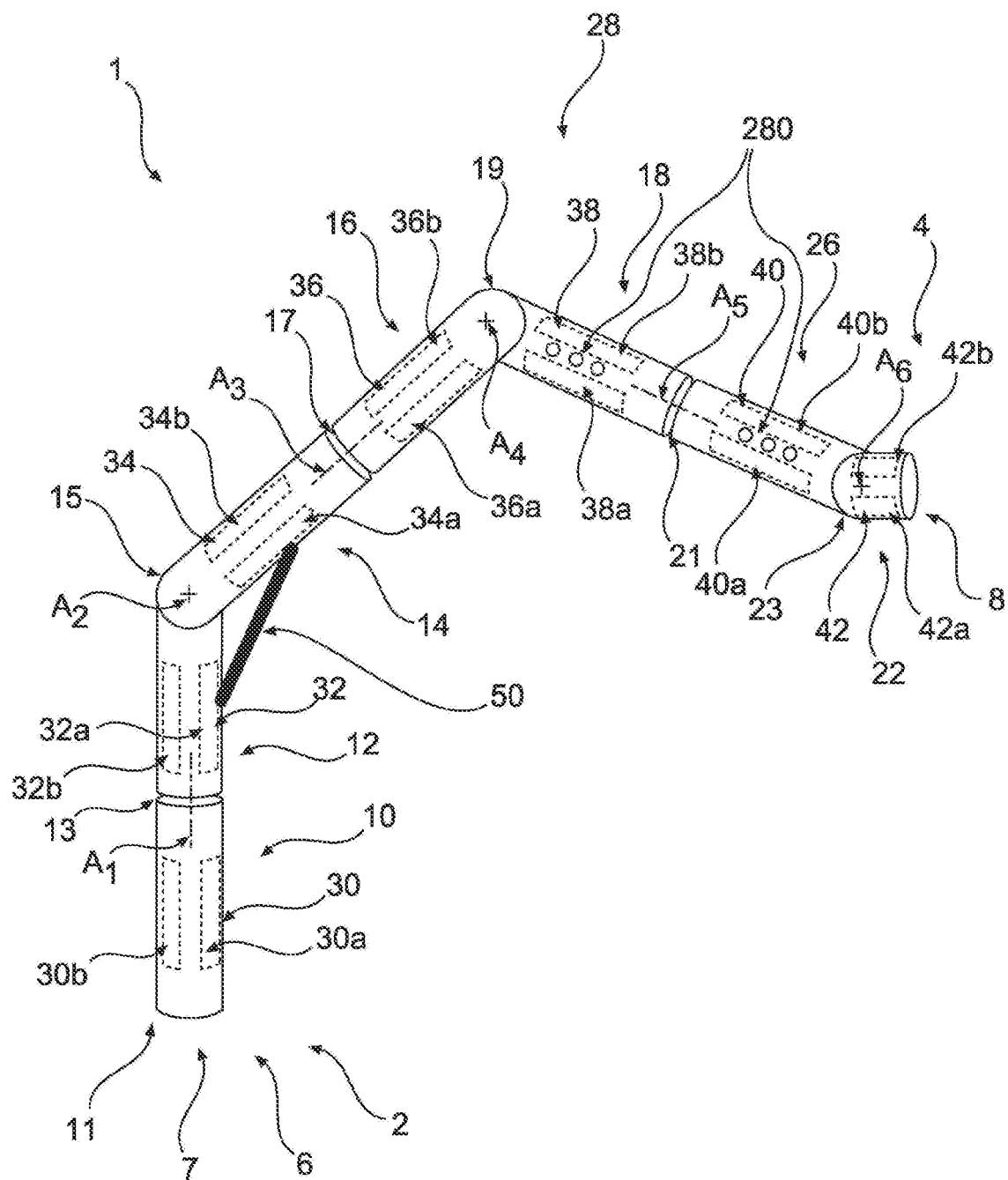
FIG. 4 shows a side view of a holding arm according to a third embodiment, in which the contacting device of the assistance operating device can be seen.

FIG. 4 shows a holding arm 1 for medical purposes, in particular for holding a surgical mechatronic assistance system and/or a surgical instrument (not shown) according to a third embodiment. Holding arm 1 has assistance operating device 280 according to the invention, which is provided here in the form of a group of buttons. In addition to the assistance operating device 280, there is also provided an arm operating device 28 by means of which at least one joint and preferably every joint 11, 13, 15, 17, 19, 21, 23 is releasable and lockable such that the holding arm 1 can be brought into a desired pose. Arm operating means 28 is preferably designed to release the associated joint (11, 13, 15, 17, 19, 21, 23) upon contact between an operator and one of the two or more arm segments (10, 12, 14, 16, 18, 20, 22). This will be explained in more detail below.

Holding arm 1 has a proximal end 2 and a distal end 4. At the proximal end 2, a base interface 6 and a mechanical interface 7 are formed. Interface 7 is used to attach holding arm 1 to a base, such as an operating table. Interface 7 is used to transfer energy and to couple holding arm 1 to an external control unit (cf. FIG. 6). At the distal end 4, a second interface 8 is provided via which it is possible to couple a mechatronic assistance system and/or a surgical instrument, such as a manipulator, to holding arm 1. A manipulator for holding and manipulating an endoscope is preferably disposed here.

The holding arm 1 according to FIG. 4 has seven arm segments 10, 12, 14, 16, 18, 20, 22, each of which is substantially rod-shaped and all of which, except for the last arm segment 22, are of substantially the same length. The seven arm segments 10, 12, 14, 16, 18, 20, 22 are each coupled to one another by means of joints 11, 13, 15, 17, 19, 21, 23, the zero-th joint 11 coupling holding arm 1 to the base (not shown in FIG. 4, see FIG. 1). In this embodiment, joints 13, 15, 17, 19, 21, 23 are all in the form of rotary joints each having one degree of freedom. According to this embodiment, the zero-th joint 11 is associated with the zero-th segment 10, the first joint 13 with the first arm segment 12, the second joint 15 with the second arm segment 14, the third joint 17 with the third arm segment 16, the fourth joint 19 with the fourth arm segment 18, the fifth joint 21 is associated with the fifth arm segment 20, and the sixth joint 23 is associated with the sixth arm segment 22. Joint 11 is designed as a translational joint, so that arm segment 10 can be extended telescopically in order to adjust the height of holding arm 1, as will be described later with reference to FIG. 8. Joints 13, 15, 17, 19, 21, 23 have respective pivot axes $A_1$, $A_2$, $A_3$, $A_4$, $A_5$, $A_6$, with respectively adjacent joints having pivot axes that are perpendicular to each other. This allows simple positioning of distal end 4 in space.

Holding arm 1 according to FIG. 4 also includes an arm operating device 28. By means of arm operating device 28, holding arm 1 can be brought into a desired pose, arm operating device 28 being adapted to release the associated joint upon contact between an operator and one of the seven arm segments. For that purpose, arm operating device 28 according to this embodiment has seven contact areas 30, 32, 34, 36, 38, 40, 42, with one contacting device 30, 32, 34, 36, 38, 40, 42 being arranged on each arm segment 10, 12, 14, 16, 18, 20, 22. A zero-th contacting device 30 is thus arranged on the zero-th arm segment 10, a first contacting device 32 on the first arm segment 12, a second contacting device 34 on the second arm segment 14, a third contacting device 36 on the third arm segment 16, a fourth contacting device 38 on the fourth arm segment 18, a fifth contacting device 40 on the fifth arm segment 20 and a sixth contacting device 42 is arranged on the sixth arm segment 22.

According to this embodiment, each contacting device 30, 32, 34, 36, 38, 40, 42 also has two contact elements 30a, 30b, 32a, 32b, 34a, 34b, 36a, 36b, 38a, 38b, 40a, 40b, 42a, 42b arranged substantially opposite one another. Contacting means 30, 32, 34, 36, 38, 40, 42 are used to detect contact between an operator and the respective arm segment 10, 12, 14, 16, 18, 20, 22. When gripping an arm segment 10, 12, 14, 16, 18, 20, 22, the operator comes into contact with the two contact elements 30a, 30b-42a, 42b, and the associated joint is released only when there is contact with both the contact elements 30a, 30b-42a, 42b of a contacting device 30-42. This means that, when the first arm segment 12 is gripped and the contact is made simultaneously with the two contact elements 32a, 32b, the first joint 13 is released by arm operating device 28. In this way, it is possible for the operator to pivot holding arm 1, or arm segments 12-22, about axis $A_1$. When one or both of the two contact elements 32a, 32b is let go of, joint 13 is locked again, and pivoting about axis $A_1$ is no longer possible. If only one of the two contact elements 32a, 32b is inadvertently touched, for example by an arm or elbow of the operator, joint 13 is not released and holding arm 1 remains in the locked state and keeps its pose.

The same applies to the second arm segment 14. In this case also, the second contacting device 34 has two contact elements 34a, 34b which are provided substantially opposite one another on the outer circumference of arm segment 14. When this arm segment 14 is gripped and contact is made with both the contact elements 34a, 34b, this contact is detected by arm operating device 28 and joint 15 associated with arm segment 14 is released. Pivoting about axis $A_2$ is now possible, so distal end 4, in FIG. 4, can be pivoted upwards or downwards. At the same time, all the other joints 13, 17, 19, 21, 23 remain locked, so no movement in them takes place.

For that purpose, arm operating device 28 may have a controller or a microprocessor which is adapted to detect contact between contact elements 30a, 30b-42a, 42b and to transmit it in the form of electrical signals.

According to this embodiment, contacting device 30, or contact elements 30a, 30b-42a, 42b, are in the form of touch-sensitive sensors and detect the pressure of contact between the operator and the respective contact element 30a, 30b-42a, 42b. Contact elements 30a, 30b-42a, 42b are preferably provided in the form of capacitive touch-sensitive sensors.

With holding arm 1 shown here, it is also possible for an operator to grip two arm segments simultaneously, for example arm segment 14 and arm segment 18, and thus to contact simultaneously contact elements 34a, 34b and 38a, 38b. Joints 15 and 19 are released as a result, and it is possible to pivot them about axis $A_2$ and also about axis $A_4$. When joints are simultaneously released in this manner, it is possible for arm segments 18 and 20 to keep their angular orientation in space, while only arm segments 34, 36 are pivoted. This means that a translational movement of the distal end 4 is also possible. In one preferred configuration of the holding arm, it is not joints 15 and 19 that are released when two arm segments are contacted simultaneously in this example with arm segments 14 and 18, but all the joints between said arm segments 14 and 18, i.e. joints 17 and 19 in this embodiment. Joint 15 remains locked. The pose of holding arm 1 can now be changed in such a way that rotation about axis A3 and axis A4 is possible. This is a particularly intuitive way of operating the holding arm. Joints 15, 17, 19 and 21 are released accordingly, for example when there is contact between the operator and holding arm segments 12 and 20.

It can also be seen in FIG. 4 that holding arm 1 has a weight compensation means 50. In this embodiment, weight compensation means 50 has a gas spring element which is coupled to arm segment 14 and arm segment 12. Alternatively, the weight compensation means may also have a cable pull and/or a equilibrated counterweight. In the case of holding arm 1 as shown in FIG. 4, the strongest torque is exerted on joint 15 about its rotational axis A2. It is therefore preferred that precisely that joint 15 be supported by means of weight compensation means 50. Thus, when joint 15 is released by contacting arm segment 14, a weight acting upon arm segment 14 due to the other arm segments 16, 18, 20, 22 and a manipulator disposed at interface 8, is supported by weight compensation means 50 so that the distal end 4 does not "sag" immediately when segment 14 is gripped.

Figure 5:
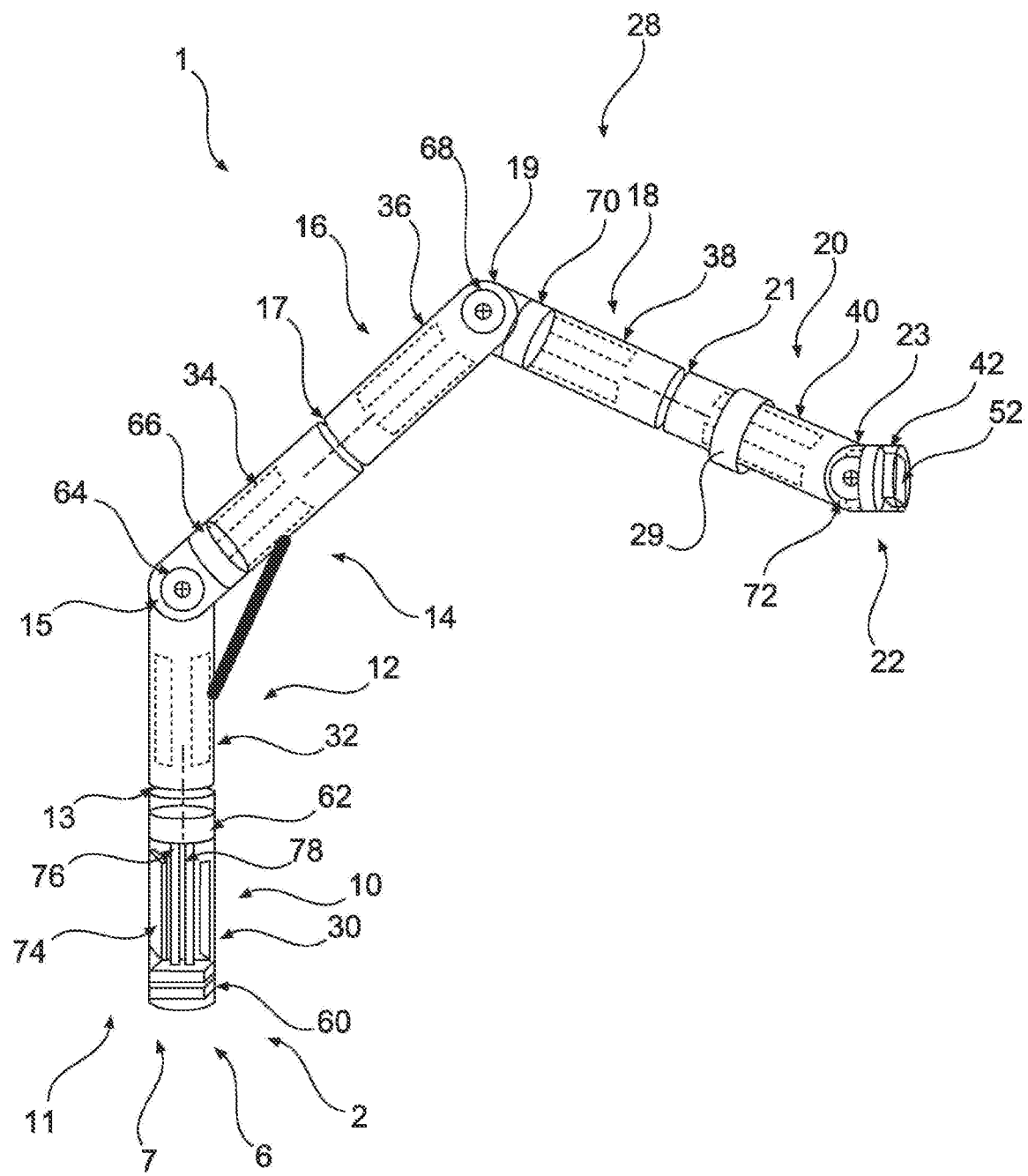
FIG. 5 shows a partly cutaway view of the holding arm shown in FIG. 4.

In addition to the elements of holding arm 1 already shown in FIG. 4, FIG. 5 shows brakes 60, 62, 64, 66, 68, 70, 72, by means of which joints 11, 13, 15, 17, 19, 21, 23 can be released and locked. Identical and similar elements are marked with the same reference signs as in FIG. 4, and reference is made in that respect to the entire description above. Although reference signs are not shown in FIG. 5 at the contact elements of contacting device 30, 32, 34, 36, 38, 40, 42, for the sake of clarity, they are nevertheless present, as can be seen by comparing FIGS. 4 and 5. In contrast to holding arm 1 of FIG. 4, holding arm 1 of FIG. 5 includes arm operating device 280 having a control ring 29.

A brake 60, 62, 64, 66, 68, 70, 72 is associated with each joint 11, 13, 15, 17, 19, 21, 23. Brake 60 is associated with joint 11, brake 62 with joint 13, brake 64 with joint 15, brake 66 with joint 17, brake 68 with joint 19, brake 70 with joint 21 and brake 72 with joint 23. All the brakes 60-72 are provided in the form of electromagnetic brakes and each comprise a permanent magnet which biases the brake into the locked state when no current is being supplied. The permanent magnet is designed in such a way that it can brake the respective joint on its own and so that the pose of holding arm 1 is held. In the zero-th arm segment 10, an electronic control unit 74 is provided. The latter is coupled via a bus system 76 (only shown in arm segment 10 in FIG. 5; cf. FIG. 7) to all the contacting devices 30-42 of operating device 28 and to all the brakes 60-72. In order to supply energy to brakes 60-72 and to contacting devices 30-42, an energy supply line 78 is also provided, which can be coupled to an energy source via interface 6 at the proximal end 2 of holding arm 1.

Figure 6:
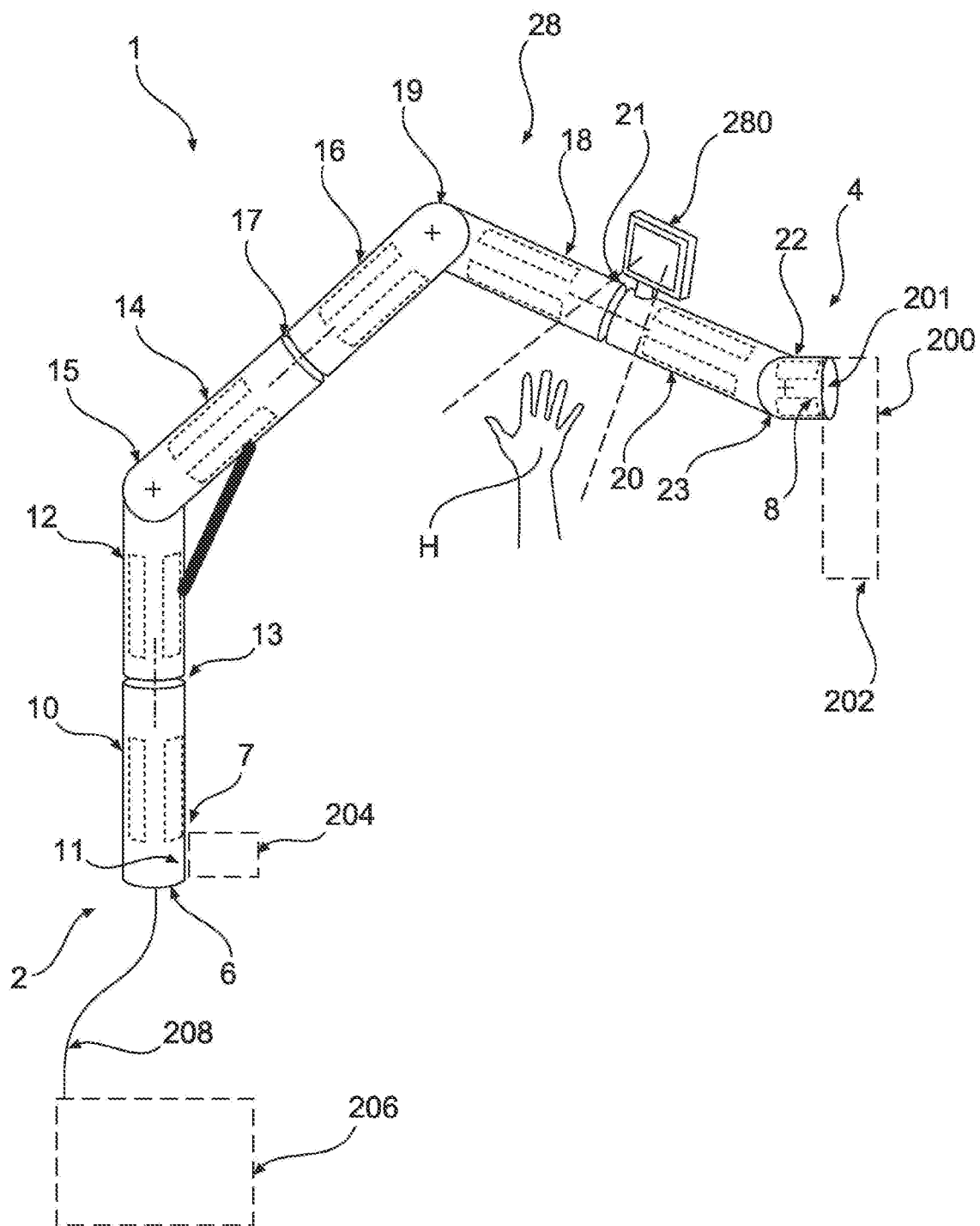
FIG. 6 shows the holding arm from FIG. 4, coupled to an external control unit and an assistance system.

FIG. 6 illustrates holding arm 1 once again, as already described with reference to FIGS. 4 and 5. According to this embodiment, holding arm 1 has a contactless assistance operating device 280 in the form of a camera with an integrated depth sensor.

In FIG. 6, holding arm 1 is shown integrated within a system. At distal end 4, by means of interface 8, a surgical mechatronic assistance system 200 is arranged which is coupled to interface 8 via an interface 201. Both the surgical mechatronic assistance system 200 and interface 201 are shown only schematically in FIG. 6. It should be understood that the surgical mechatronic assistance system 200 may be provided in the form of an endoscope, for example, or as a laparoscope or the like. Assistance system 200 has a working section 202, which can be the tip of the endoscope, for example. At proximal end 2, holding arm 1 according to FIG. 6 is coupled to a base 204 via mechanical interface 7. Base 204 is shown here likewise in schematic form only. It may be provided in the form of a standard rail of an operating table, for example.

According to this embodiment, first interface 6 is coupled to an external control unit 206. For that purpose, interface 6 is connected by means of a cable 208 to external control unit 206. According to this embodiment, external control unit 206 is provided in the form of an OP system comprising, for example, a conventional computer and an input-output interface for operating the OP system. The OP system preferably has software components which are configured to store and process data transmitted from holding arm 1 at interface 6.

Depending on the configuration of interface 6, the interface may communicate wirelessly with OP system 206, for example via Bluetooth®, Wi-Fi® or similar.

Figure 7:
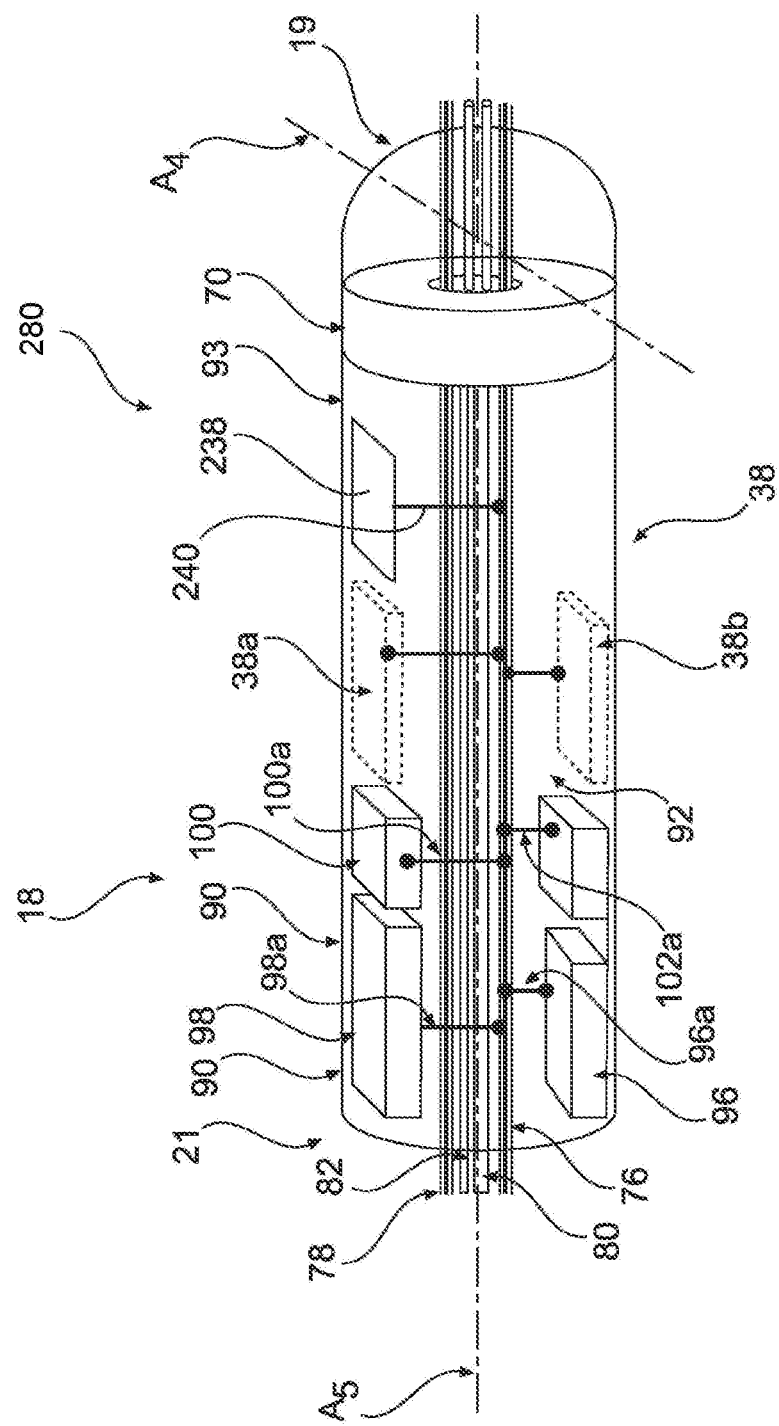
FIG. 7 shows a schematic view of an arm segment, illustrating the transmission means.

FIG. 7 shows an embodiment of an arm segment, in which the fourth arm segment 18 is shown. It should be realised that the other arm segments 10, 12, 14, 16, 20, 22 may be configured the same way. Arm segment body 90 has a hollow space 92 inside, in which various elements such as brake 70 are arranged. Joints 19, 21 and the two pivot axes $A_4$, $A_5$ of joints 19, 21, which interact with holding arm segment 18, are shown schematically in FIGS. 4 and 5. Joint 19 is associated with holding arm segment 18. Arm segment body 90 has an outer surface 93 which is substantially cylindrical. Arm segment body 90 is made, for example, of a metal such as aluminium or titanium, an aluminium- or titanium-based alloy, or a composite fibre material such as GRP or CFRP, and is preferably of lightweight construction.

According to FIG. 7, arm segment 18 has an assistance operating device 280 with contacting device 238 provided in the form of a touch-sensitive sensor array, said contacting device being coupled via a data interface 240 to the bus system 76 of holding arm 1.

According to FIG. 7, arm segment 18 has a contacting device 38 which is part of arm operating device 28 (cf. FIGS. 4, 5 and 6). Contacting means 38 has two contact elements 38a, 38b, which are provided in the form of touch-sensitive sensors and which are arranged flush with the outer surface 93 of arm segment 18. The two contact elements 38a, 38b are arranged substantially opposite one other relative to axis $A_5$, so that an operator comes into contact with both the contact elements 38a, 38b when gripping arm segment 18, as described above.

The two contact elements 38a, 38b are coupled by means of lines 94a, 94b to bus system 76. Contact elements 38a, 38b are coupled via bus system 76 to the electronic control unit 74 and via the latter to brake 70, so that brake 70 is released by arm operating device 28 when an operator comes into contact with contact elements 38a, 38b.

In addition to bus system 76, an energy transmission system 78 and a cable channel 80 and a working channel 82 are arranged inside arm segment body 90. By means of energy transmission system 78, contact elements 38a, 38b and brake 70 are connected to an energy supply.

Alternatively or additionally, an electronics module 96 which is coupled to bus system 76 via a line 96a is disposed inside each arm segment. In such a case, contact elements 38a, 38b, which are connected via line 94a, 94b to data bus 76, interact only with electronics module 96, which converts the contact detected by contact elements 38a, 38b into a control signal for brake 70 and sends said control signal via bus system 76 to brake 70 in order to release joint 19. If such an electronics module 96 is disposed inside each arm segment, holding arm 1 has a substantially modular structure, and the individual arm segments 10-22 are independent of the electronic control unit 74 which is disposed in proximal arm segment 10.

Cable channel 80 is used to guide cables running from the proximal end 2 to the distal end 4 to supply interface 8, in particular. Working channel 82 is used to receives tubes or waveguides and the like as may be required by that particular kind of manipulator disposed at interface 8. If, for example, an endoscope is disposed at interface 8, a waveguide which can transmit an image recorded by an endoscopic camera is preferably guided through working channel 82. Working channel 82 is thus used to receive transmission means appropriate to the particular field of application.

There is also a sensor 98 disposed inside arm segment 18. A sensor is preferably disposed in each arm segment 10-22, and it should be understood that the sensors in arm segments 10, 12, 14, 16, 20 and 22 may be configured in the same way as sensor 98 in arm segment 18. Sensor 98 is preferably provided in the form of an acceleration sensor. By providing such an acceleration sensor in each arm segment, it is possible to determine the pose of holding arm 1 at any time. For that purpose, sensor 98 is coupled via line 98a to data bus 76, so that the data captured by sensor 98 are transmitted to the electronic control unit 74, which then determines the pose of holding arm 1 from all the sensor data from all the arm segments. By providing such a sensor 98, it is also possible to determine the absolute and relative position of an end effector or manipulator disposed at interface 8. If holding arm 1 is attached to an operating table, it is also possible to detect any movement of the operating table. If all the sensors in all the arm segments detect a movement in the same direction, this is an indication that the entire holding arm 1 has been moved while keeping its pose, for example by the operating table or a plate of the operating table having been rotated or displaced relative to a pillar of the operating table. Such movement can also be detected by means of sensors 98. External impulses, such as jolts against holding arm 1, can also be detected.

According to FIG. 7, a processor unit 100 assigned to assistance operating device 280 is provided in arm segment 18 and is coupled to data bus 76 via line 100a.

Figure 8:
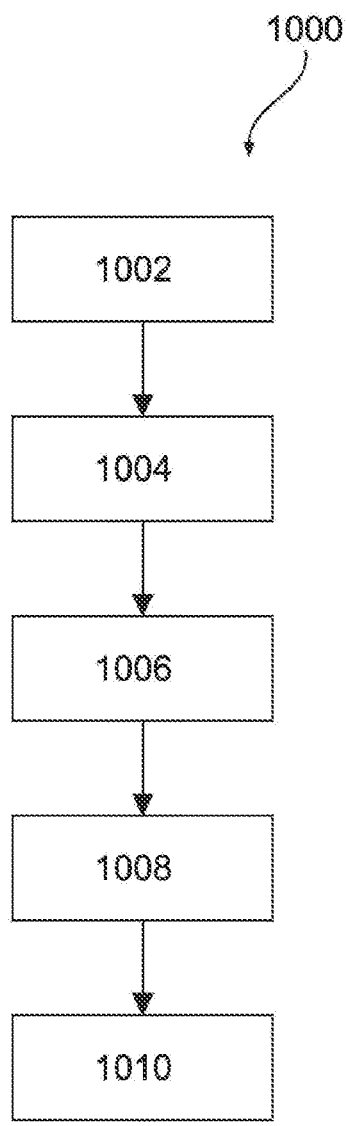
FIG. 8 shows a flow diagram of a method according to the invention.

FIG. 8 shows a method 1000 according to the invention for controlling a surgical mechatronic assistance system coupled to a holding arm for medical purposes (see FIGS. 1-6)

In a first step 1002, an operator action by an operator is detected, which is directed at controlling the assistance system by means of an operating device arranged on the holding arm.

In a second step 1004, sensor data and workspace data relating to the holding arm are fetched 1004 via the transmission means.

In a third step 1006, the detected operator action is translated into a data structure, taking into account the sensor data relating to the holding arm, and the request signal is generated from the data structure.

This is followed, in a fourth step 1008, by detecting whether the surgical mechatronic assistance system would remain within a permitted workspace when driven in accordance with the request signal.

In a fifth step 1010, a request signal representing the operator action is transmitted to the assistance interface for the purpose of controlling the surgical mechatronic assistance system.

The method is preferably performed with a holding arm 1 according to one of the preferred embodiments of holding arm 1 described in the foregoing (FIGS. 1-7).

The invention claimed is:

1. A holding arm for holding a surgical mechatronic assistance system, the holding arm comprising:
   a proximal end for attaching the holding arm to a base and a distal end;
   a base interface at the proximal end for connecting the holding arm to an external control unit for transmitting signals to and from the holding arm;
   an assistance interface at the distal end for coupling the holding arm to the surgical mechatronic assistance system and to control the surgical mechatronic assistance system;
   a transmission means arranged inside the holding arm that transmits signals between the assistance interface and the base interface;
   an assistance operating device on the holding arm, the assistance operating device comprising at least two contact mechanisms configured to be contacted by an operator to receive an operator action for controlling the surgical mechatronic assistance system and to cause a request signal representing the operator action to be transmitted to the assistance interface for controlling the surgical mechatronic assistance system only when the operator contacts two of the contact mechanisms simultaneously; and
   a processor unit configured to translate the operator action into a data structure, wherein the data structure comprises a 3D motion vector and a velocity value.

2. The holding arm of claim 1, wherein the processor unit is coupled at least temporarily to the transmission means and is configured to fetch sensor data and/or workspace data relating to the holding arm from the transmission means.

3. The holding arm of claim 2, wherein the processor unit is configured to take the sensor data relating to the holding arm into account when translating the operator action into the data structure.

4. The holding arm of claim 1, wherein the processor unit is configured to convert the data structure into the request signal.

5. The holding arm of claim 1, wherein the processor unit is configured to detect whether the surgical mechatronic assistance system would remain within a permitted workspace when driven in accordance with the request signal.

6. The holding arm of claim 5, wherein the processor unit is configured to cause the request signal to be transmitted to the surgical mechatronic assistance system only if the surgical mechatronic assistance system would remain within the permitted workspace when driven in accordance with the request signal.

7. The holding arm of claim 5, wherein the assistance operating device comprises signalling means for emitting a warning signal which is perceptible to the operator, and the processor unit is configured to activate the signalling means if the surgical mechatronic assistance system would leave the permitted workspace or would approach a workspace boundary to within a predefined distance when driven in accordance with the request signal.

8. The holding arm of claim 7, wherein the signalling means comprises a vibration module and/or a visual display module.

9. The holding arm of claim 1, wherein the assistance operating device comprises at least one control ring which is arranged around the circumference of at least one arm segment and is axially mobile.

10. The holding arm of claim 1, wherein the contacting mechanisms are pushbuttons.

11. The holding arm of claim 1, wherein the contacting mechanisms are touch-sensitive sensors.

12. The holding arm of claim 1, wherein the assistance operating device comprises a camera and/or a distance sensor for detecting the operator action contactlessly.

13. The holding arm of claim 12, wherein the contacting mechanisms and the camera and/or the distance sensor are provided in redundant form, and the processor unit is configured to verify whether the operator action directed at controlling the surgical mechatronic assistance system is actually being performed.

14. The holding arm of claim 1, wherein the transmission means comprises a bus system.

15. The holding arm of claim 1, further comprising two or more arm segments and two or more joints, wherein the arm segments are connected to each other by joints.

16. The holding arm of claim 15, further comprising an arm operating device by which at least one joint is releasable and lockable such that the holding arm can be brought into a desired pose, wherein the arm operating device is configured to release the associated joint upon contact between the operator and one of the two or more arm segments.

17. The holding arm of claim 1, further comprising an arm operating device configured to release and lock the holding arm, the arm operating device comprising at least two contact pads configured to be contacted simultaneously by the operator for releasing the holding arm so it can be brought into a desired pose.

18. A method for controlling a surgical mechatronic assistance system coupled to a holding arm for medical purposes, said method comprising:
  detecting an operator action at least two contact mechanisms on the holding arm by an operator for controlling the surgical mechatronic assistance system via at least two contact mechanisms of an operating device arranged on the holding arm;
  transmitting a request signal representing the operator action to an assistance interface for controlling the surgical mechatronic assistance system only when the operator contacts two of the contact mechanisms simultaneously;
  translating the detected operator action into a data structure, wherein the data structure comprises a 3D and a velocity value; and
  generating the request signal from the data structure.

19. The method of claim 18, further comprising requesting sensor data and/or workspace data relating to the holding arm.

20. The method of claim 19, further comprising translating the detected operator action into the data structure based on the sensor data relating to the holding arm.

21. The method of claim 18, further comprising detecting whether the surgical mechatronic assistance system would remain within a permitted workspace when driven in accordance with the request signal.

22. The method of claim 21, further comprising transmitting the request signal to the surgical mechatronic assistance system if the surgical mechatronic assistance system would remain within the permitted workspace when driven in accordance with the request signal.

23. The method of claim 21, further comprising filtering the request signal if the surgical mechatronic assistance system would leave the permitted workspace when driven in accordance with the request signal.

24. The method of claim 21, further comprising emitting via the operating device a warning signal which is perceptible to the operator if the permitted workspace for the surgical mechatronic assistance system is restricted.

25. The method of claim 18, further comprising filtering the request signal insofar as the surgical mechatronic assistance system would leave a permitted workspace when driven in accordance with the request signal.

26. The method of claim 18, further comprising determining whether the operator action detected via the operating device is directed at releasing the holding arm or movement of the surgical mechatronic assistance system.

27. The method of claim 18, wherein the operator action is a gesture by the operator.

28. A holding arm for holding a surgical mechatronic assistance system, the holding arm comprising:
  a proximal end for attaching the holding arm to a base and a distal end;
  a base interface at the proximal end for connecting the holding arm to an external control unit for transmitting signals to and from the holding arm;
  an assistance interface at the distal end for coupling the holding arm to the surgical mechatronic assistance system and to control the surgical mechatronic assistance system;
  a transmission means arranged inside the holding arm that transmits signals between the assistance interface and the base interface;
  an arm operating device configured to release and lock the holding arm, the arm operating device comprising at least two contact pads configured to be simultaneously contacted by an operator for releasing the holding arm so it can be brought into a desired pose;
  an assistance operating device on the holding arm, the assistance operating device configured to detect an operator action for controlling the surgical mechatronic assistance system and to cause a request signal representing the operator action to be transmitted to the assistance interface for controlling the surgical mechatronic assistance system, the assistance operating device comprising at least one control ring which is rotatable about an axis for inputting said operator action; and
  a processor unit in electrical communications with the control ring, the processor unit being configured to translate the operator action into a data structure, wherein the data structure comprises a 3D motion vector and a velocity value.

29. A holding arm for holding a surgical mechatronic assistance system, the holding arm comprising:
- a proximal end for attaching the holding arm to a base and a distal end;
- a base interface at the proximal end for connecting the holding arm to an external control unit for transmitting signals to and from the holding arm;
- an assistance interface at the distal end for coupling the holding arm to the surgical mechatronic assistance system and to control the surgical mechatronic assistance system;
- two or more arm segments and two or more joints, wherein the arm segments are connected to each other by the joints;
- an arm operating device by which at least one joint is releasable and lockable such that the holding arm can be brought into a desired pose, the arm operating device includes at least a first pair of associated contact pads at a first arm segment of said two or more arm segments and a second pair of associated contact pads at a second arm segment of said two or more arm segments, wherein the arm operating device is configured to release a first joint of said two or more joints upon contact between an operator and said first pair of contact pads, and to release a second joint of said two or more joints upon contact between the operator and said second pair of contact pads;
- a transmission means arranged inside the holding arm that transmits signals between the assistance interface and the base interface;
- an assistance operating device configured to detect an operator action for controlling the surgical mechatronic assistance system and to cause a request signal representing the operator action to be transmitted to the assistance interface for controlling the surgical mechatronic assistance system; and
- a processor unit assigned to the assistance operating device and configured to translate the operator action into a data structure, wherein the data structure comprises a 3D motion vector and a velocity value.

* * * * *